(12) United States Patent
Richards

(10) Patent No.: US 6,926,677 B2
(45) Date of Patent: Aug. 9, 2005

(54) CELLULAR COLLECTION APPARATUS AND METHOD

(76) Inventor: Michael Owen Richards, 1423 Palmetto Rd., Veroma, MS (US) 38879

(*) Notice: Subject to any disclaimer, the term of this patent is extended or adjusted under 35 U.S.C. 154(b) by 125 days.

(21) Appl. No.: 10/122,963

(22) Filed: Apr. 11, 2002

(65) Prior Publication Data

US 2002/0111562 A1 Aug. 15, 2002

Related U.S. Application Data (63) Continuation-in-part of application No. 09/721,026, filed on Nov. 21, 2000, now Pat. No. 6,402,700.
(60) Provisional application No. 60/167,099, filed on Nov. 23, 1999.

(51) Int. Cl.[7] ............................................. A61B 10/00
(52) U.S. Cl. ................................................... 600/562
(58) Field of Search ...................... 600/562, 569–574, 600/576, 581, 582, 184, 208, 219–223; 606/119, 157

(56) References Cited

U.S. PATENT DOCUMENTS

| | | | |
|---|---|---|---|
| 4,136,680 A | * | 1/1979 | Southworth ................ 600/572 |
| 4,620,548 A | | 11/1986 | Hasselbrack |
| 4,628,941 A | | 12/1986 | Kosasky |
| 4,867,176 A | | 9/1989 | Lash |
| 5,108,408 A | * | 4/1992 | Lally .......................... 606/119 |
| 5,121,752 A | | 6/1992 | Canna |
| 5,722,983 A | | 3/1998 | Van Der Weegen |
| 5,746,215 A | * | 5/1998 | Manjarrez ................... 600/573 |
| 5,787,891 A | | 8/1998 | Sak |
| 5,951,550 A | | 9/1999 | Shirley et al. |
| 6,036,638 A | | 3/2000 | Nwawka |
| 6,302,853 B1 | | 10/2001 | Sak |
| 6,352,513 B1 | * | 3/2002 | Anderson et al. ........... 600/572 |
| 6,394,966 B1 | * | 5/2002 | Gill et al. ................... 600/569 |
| 6,402,700 B1 | * | 6/2002 | Richards ..................... 600/562 |
| 6,616,603 B1 | * | 9/2003 | Fontana ...................... 600/184 |

OTHER PUBLICATIONS

Cervical Cancer: Backgrounder, National Cancer Institute, Feb. 22, 1999, (7 pages).
David M. Eddy, MD, PHD, Screening for Cervical Cancer, in Common Screening Tests, 1991, pp. 255–283, American College of Physicians, Philadelphia, Pennsylvania.

* cited by examiner

*Primary Examiner*—Max F. Hindenburg
*Assistant Examiner*—Brian Szmal
(74) *Attorney, Agent, or Firm*—Charlotte W. Catlett (57) ABSTRACT

A personal cellular collection apparatus and method for collecting a non-intrusive cell or tissue sample for medical testing such as cervical cancer screening is provided. The apparatus includes a cervical guide ring, an insertion handle, a means for movably attaching the guide ring, and a means for directing a tissue sampling tool to a woman's cervix. The means for movably attaching the guide ring to the insertion handle is a hinge or rachet mechanism having a tab or latch on the ring and a catch on the proximal end of the insertion handle. The method of the invention includes insertion of the collection tool through the introitus of the user's vagina, digital positioning of the guide ring to encircle the user's cervix, guiding a sampling tool to the cervix, wiping the cervix with the sampling tool to collect a tissue sample and removing the sampling tool and cervical guide from the user's vagina.

11 Claims, 7 Drawing Sheets

FIG. 15

CELLULAR COLLECTION APPARATUS AND METHOD

CROSS-REFERENCE TO RELATED APPLICATIONS

This application is a continuation-in-part of U.S. application Ser. No. 09/721,026, filed on Nov. 21, 2000, entitled Pap Smear Apparatus and Method, now issued as U.S. Pat. No. 6,402,700, which is related to the provisional application Ser. No. 60/167,099, filed on Nov. 23, 1999, entitled Pap Smear Apparatus and Method.

BACKGROUND OF THE INVENTION

1. Field of the Invention

This invention relates to gynecological medical devices, and more particularly to a medical tool and method for enabling a woman to collect a cervical cell or other biological material sample for use during a screening test for cancer and infections of the cervix.

2. Description of Related Art Including Information Disclosed Under 37 CFR 1.97 and 37 CFR 1.98

The Papanicalou (PAP) test, commonly known as a PAP smear, is an important routine gynecological test usually done annually in sexually active females to screen for cervical cancer. The tests known in the art typically require an in office visit with a gynecologist where the doctor takes a cellular sample of the cervix for lab analysis. Current medical practice requires a gynecologist to insert a speculum into the patient's vagina to access the cervix for tissue sample collection. Many women find this method an uncomfortable, intrusive exam, and opt to not have the routine screening performed.

While certain groups of women are recognized to be at a higher risk for cervical cancer and exposure to a variety of Human Papilloma Virus subtypes, many monogamous women do not fall into the high risk categories. For these women, the screening guidelines recommend testing every three years after three normal annual PAP smears. *Cervical Cancer: Backgrounder*, National Cancer Institute, Feb. 22, 1999. For many women, the routine screening test would be regularly performed if it could be done in a non-intrusive, private manner. *Screening for Cervical Cancer*, in Common Screening Tests, David M. Eddy, MD, PhD, Editor, Chapter 10, pages 255-283 (1991).

Of particular relevance to the instant invention is U.S. Pat. No. 5,121,752 to Canna. Canna '752 discloses a self-obtaining PAP smear apparatus which must be used by a woman standing in an upright position. The apparatus includes a rigid, cylindrical speculum, angled endocervical sampler and an elongated angled spatula. The cylindrical speculum includes an angled front orifice designed to fit about the cervix. After insertion, a mirror is used for visual observation to affirm correct placement of the orifice around the cervix. In actual practice, however, obtaining a clear view by speculum of the cervix is difficult even under direct vision. In addition, the length and rigidity of the speculum prevent the use of digital assistance to confirm proper placement.

Although the aforementioned reference discloses one method and apparatus for self-obtaining PAP smears, it fails to teach or disclose an efficient, easy to use method and apparatus that enables digital location of the cervix for accurate placement of the speculum and reliable sampling of the cervical tissue. The present invention meets these needs. The invention provides an efficient tool for privately performing a non-intrusive PAP smear or tissue sample collection without the need for assistance by a gynecologist or other medical practitioner.

BRIEF SUMMARY OF THE INVENTION

The present invention is a cellular collection apparatus and method of use for enabling a user to obtain a personal PAP smear or similar tissue sample. The apparatus of the invention includes a cervical guide ring, an insertion handle, a means for movably attaching the guide ring to the insertion handle, and a means for guiding a tissue sampling tool to the woman's cervix.

In a preferred embodiment, the means for movably attaching the guide ring to the insertion handle is a hinge mechanism. In one aspect, the hinge mechanism includes a tab on the guide ring that engages with a catch tab proximal to the first end of the insertion handle when the tool is in use.

In another embodiment, the means for movable attaching the guide ring to the insertion handle is a ratchet mechanism. In one aspect, the ratchet mechanism includes a pawl and spur. In yet another aspect, the pawl is on the guide ring and the spur is on the insertion handle. In still another aspect, the rachet mechanism includes at least one tooth on the guide ring and a catch proximal to the first end of the insertion handle.

In another preferred embodiment of the invention, the apparatus includes a means for guiding a tissue sampling tool to the woman's cervix. In one aspect of the invention, the sampling tool guidance means includes a longitudinal groove in the length of the insertion handle which mates with a slidable extension such as a dove-tail or T-slide. In one aspect, the slide is on the sampling tool. In another aspect, the slide is on the housing for the sampling tool. In yet another aspect, the slidable extension of the sampling tool is placed within the longitudinal groove of the handle to secure the path of the sampling tool directly to the cervix.

In another embodiment of the invention, the insertion handle includes a longitudinal bore open at the first and second ends. The first end is proximal to the ring and cervix, while the second end is distal. During use, one or more sampling tools are directed to the cervix through the bore of the insertion handle.

It is another object of the invention to provide a method for enabling a user to obtain a biological material cell sample or PAP smear without the aid of a gynecologist or other medical professional. The method includes the steps of inserting a cervical guide tool into the user's vagina, positioning a guide ring around the user's cervix, guiding a sampling tool through the introitus of the user's vagina to the cervix; and wiping the endocervical canal and surrounding surface areas with one or more sampling tools. Once the sampling is completed, the tools are removed from the user's vagina, and the samples are sealed in a fixative for later analysis.

The step of positioning the guide ring around the user's cervix includes digital palpation of the cervix to properly place the ring, thereby capturing the cervix in the ring's center. In another aspect of the invention, the step of guiding the sampling tool to the cervix includes the step of slidably mating an extension on the sampling tool to a groove in the handle of the cervical guide tool. In another aspect, the guidance step includes the step of directing one or more sampling tools to the cervix through a longitudinal bore in the insertion handle of the cervical guide tool.

BRIEF DESCRIPTION OF THE SEVERAL VIEWS OF THE DRAWINGS

The invention will be better understood and its numerous objects and advantages will become more apparent to those skilled in the art by reference to the following drawings, in conjunction with the accompanying specification, in which.

DETAILED DESCRIPTION OF THE INVENTION

The present invention is a personal cellular collection apparatus and method for collecting a non-intrusive cell or tissue sample for medical testing such as a PAP smear or cervical cancer screening. Referring to FIGS. 1–4 of the drawings, the apparatus of the invention 10 includes a cervical guide ring 12, an insertion handle 20, a means for movably attaching ring 12 to handle 20, and a means for guiding a tissue sampling tool to the woman's cervix.

Cervical guide ring 12 includes an upper section 14, a lower section 16, a central aperture 15, and an optional recess 18. Insertion handle 20 includes a proximal first end 22, a distal second end 28, and an optional longitudinal groove 26 having open end 28 and closed end 29.

Figure 1:
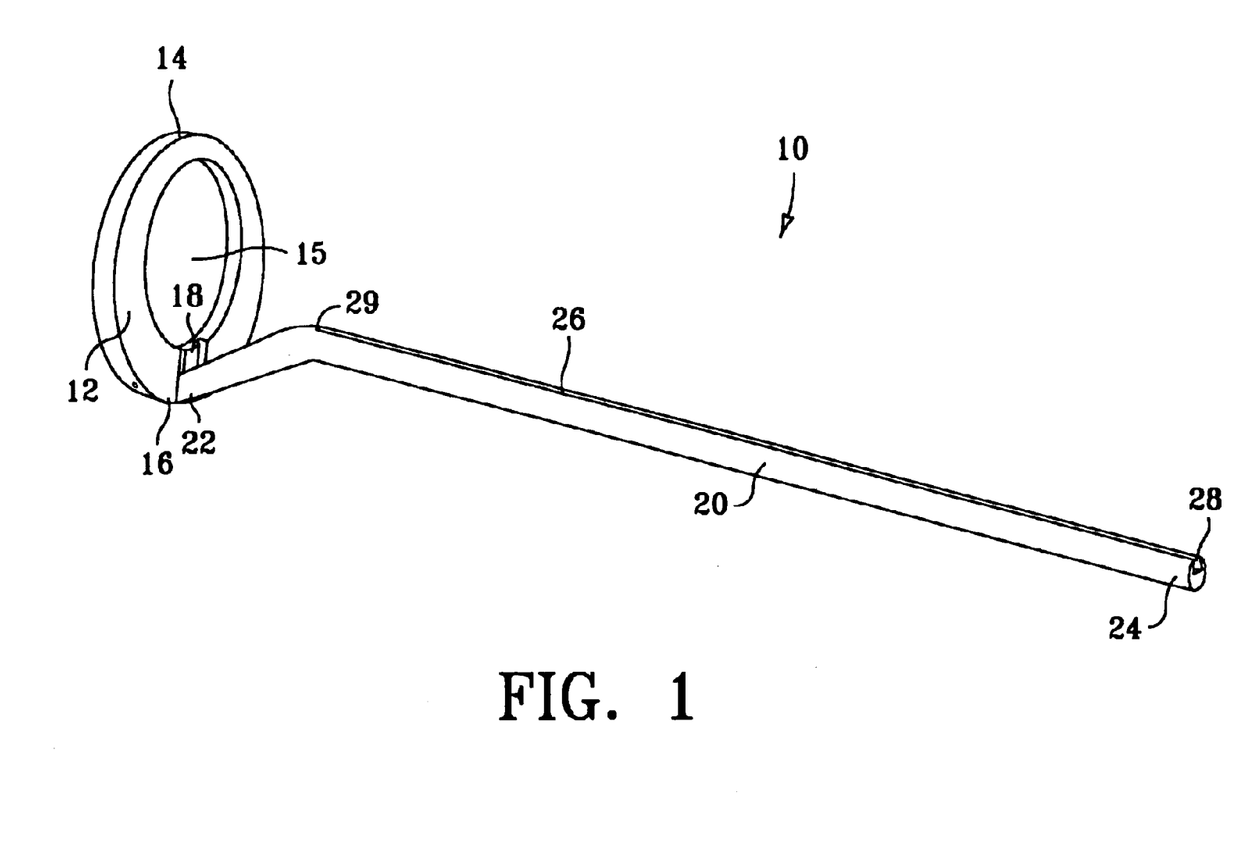
FIG. 1 is a perspective view of an embodiment of the cellular collection apparatus, depicting the guide ring in the vertical, sample collection position.
Figure 2:
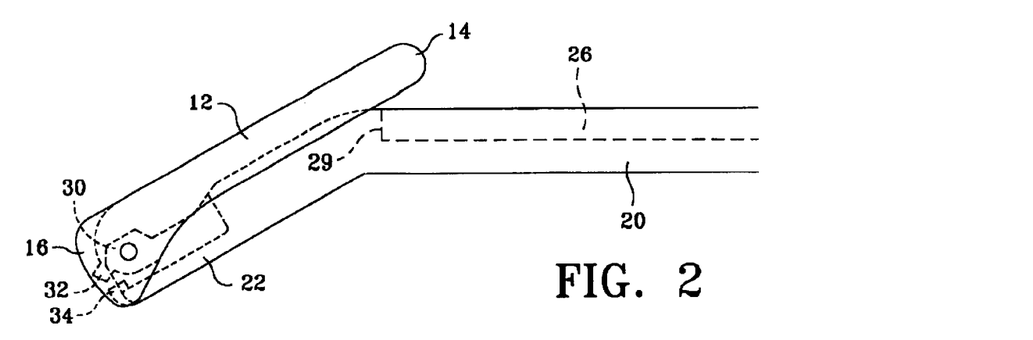
FIG. 2 is a side elevation view of the embodiment of the present invention shown in FIG. 1, depicting the guide ring in the folded insertion position.

In a preferred embodiment as shown in FIGS. 1–4, the means for movably attaching ring 12 to handle 20 is hinge or ratchet mechanism 30 including tab 32 proximal to lower ring section 16 and catch tab 34 at end 22 of insertion handle 20. When the collection apparatus is in the folded, insertion position, parts 32, 34 of hinge mechanism 30 are not engaged as shown in FIG. 2. In the design depicted in FIGS. 1–4 of the drawings, recess 18 permits ring 12 to lay flush against end 22 of handle 20 when the apparatus is folded for insertion.

It will be understood and appreciated by one skilled in the art that there are other ratchet and hinge means known in the art which may be suitable for use with the present invention. Specifically, other mechanisms known in the art may be modified or adapted to permit moveable mounting of the guide ring 12 to the insertion handle 20 to allow the user to change the guide ring 12 between folded, vertical and horizontal positions. It will also be apparent to those skilled in the art that these various designs of hinge or ratchet means known in the art and readily adaptable for use in the present invention would not always require the inclusion of a recess 18 to fold ring 12 against end 22 of handle 20.

Figure 3:
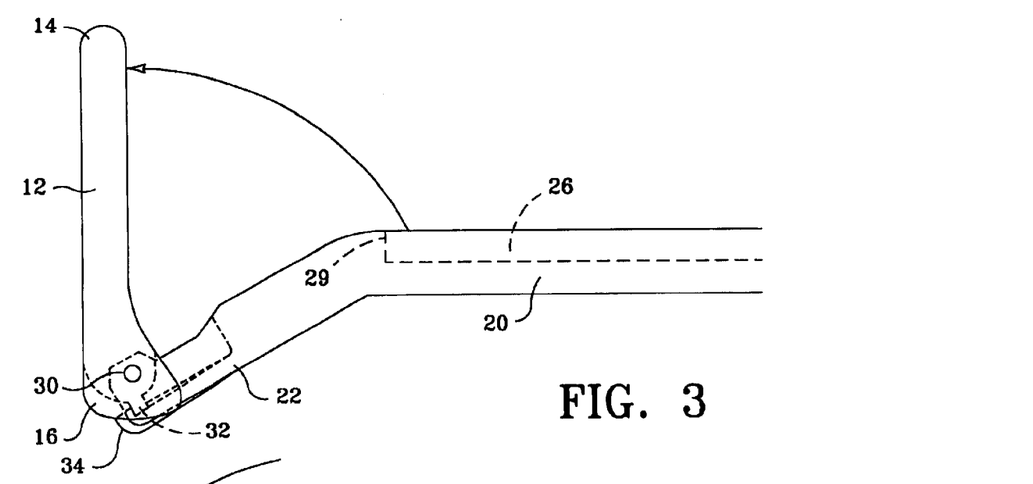
FIG. 3 is a side elevation view of the embodiment of the present invention shown in FIG. 1, depicting the guide ring in the vertical sampling position.
Figure 4:
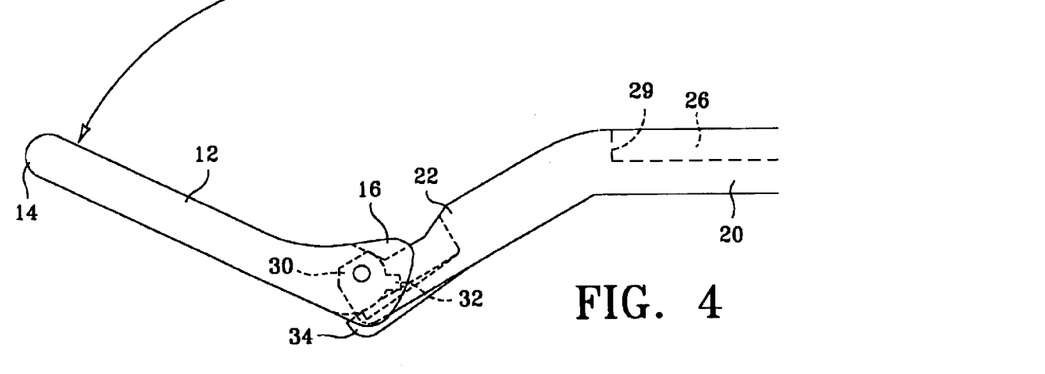
FIG. 4 is a side elevation view of the embodiment of the present invention shown in FIG. 1, depicting the guide ring in the substantially horizontal removal position.

When ring 12 is raised during use to the vertical sampling position, the one-way ratchet 30 shown in FIGS. 1–7 clicks into position and prevents ring 12 from returning to the folded position against handle 20 during use. Specifically, as shown in FIG. 3, catch tab 34 engages tab 32 to secure ring 12 in the vertical position during use. During sampling, the user may continue to hold end 24 of handle 20 to secure ring 12 in position at the cervix if needed. After the tissue sampling is completed, the user may pull out handle 20 of apparatus 10 to disengage tabs 32, 34 of mechanism 30, causing guide ring 12 to move to a substantially horizontal position as shown in FIG. 4.

It will be understood and appreciated by those skilled in the art that all or part of collection apparatus 10 may be constructed of a reusable, pliable material. When handle 20 is constructed of a pliable material, ring 12 may be returned to the folded, insertion position after use by flexing tab 34 down away from tab 32.

Referring now to FIGS. 1, and 6–8, one means for guiding a tissue sampling tool to the user's cervix is shown and includes sampling tool assembly 40 and longitudinal groove 26 on handle 20. Sampling tool assembly 40 includes tool housing 44 having a collection tool casing 41, extension 42, and a longitudinal bore 46. It will be apparent to one skilled in the art that any number of conventional tab extensions 42 may be used, such as dove-tailed or T-slide designs, as long as extension 42 movably mates within longitudinal groove 26 of handle 20.

Figure 5:
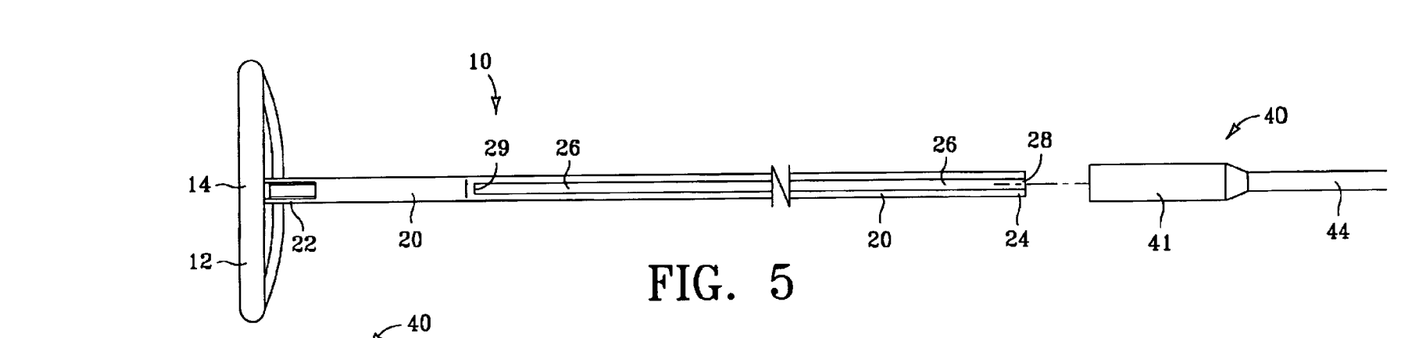
FIG. 5 is a top plan view of the cellular collection apparatus, depicting a sampling tool housing with a retracted collection tool for use with the present invention.
Figures 6, 7, 8:
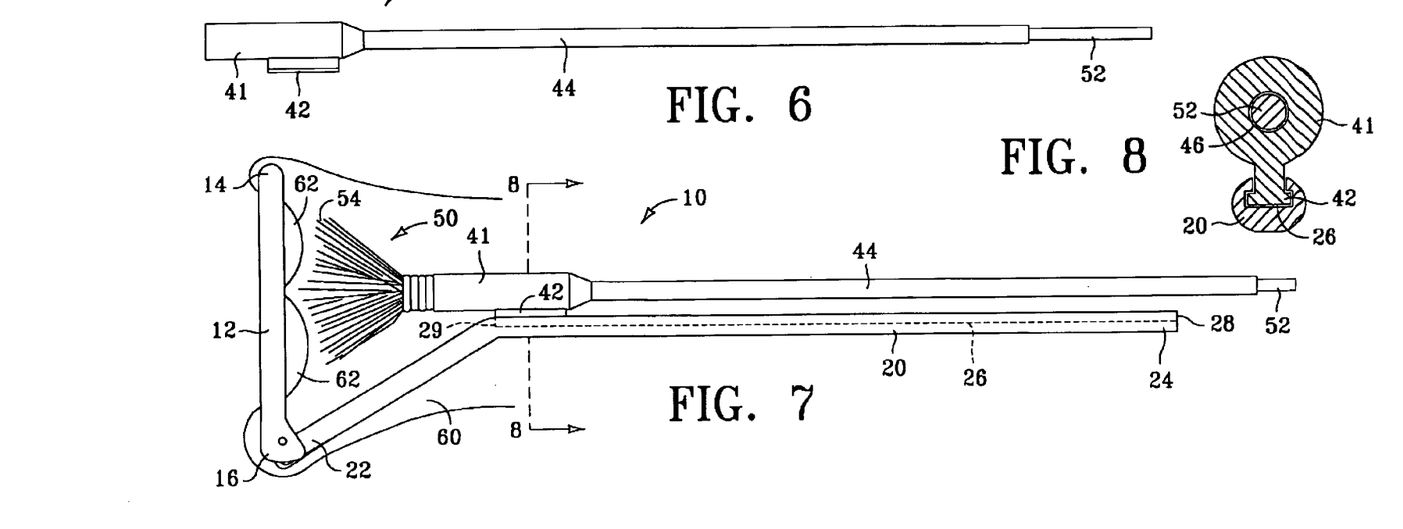
FIG. 6 is a side plan view of the sampling tool and housing shown in FIG. 5, depicting a slide mechanism.
FIG. 7 is a side elevation view of the collection apparatus of the present invention, depicting a collection brush sampling tool extended from a tool housing.
FIG. 8 is a cross-sectional view of the collection apparatus taken along line 8—8 of FIG. 7.
Figure 9:
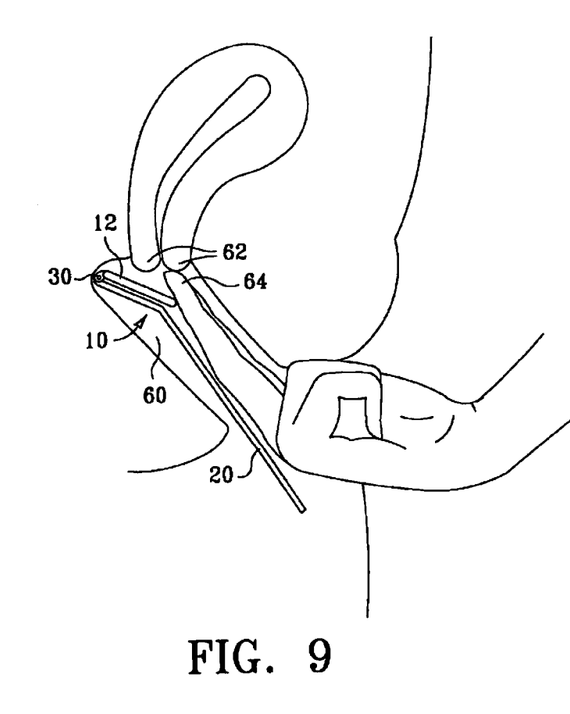
FIG. 9 is a side view of an embodiment of the present invention shown inserted in the user's vagina, having the guide ring in the folded insertion position, with the user digitally locating the cervix.

A collection brush 50 is shown retracted in FIGS. 5 and 6 with handle 52 protruding through bore 46 of housing 44. When retracted within housing 41, housing 41 serves the additional function of protecting the sampling tool 50 from contamination with non-cervical cells during use.

In this preferred embodiment, longitudinal groove 26 has an open access end 28 at distal end 24 and a closed stop 29 proximal to handle end 22. During use of the present invention, extension 42 of housing 41 is slidably mated with longitudinal groove 26 of handle 20. Specifically, after insertion of the collection apparatus in the user's vaginal, extension 42 of sampling tool assembly 40 is inserted into groove 26 at open end 28 and slidably moved forward along groove 26 until part 42 meets stop 29. In this position, housing 41 rests proximal to the user's cervix 62. As shown in FIG. 7, when brush handle 52 is moved forward, collection bristles 54 advance out of protective housing 41, into direct contact with cervix 62.

The use and operation of the present invention will be best understood in conjunction with the method of the invention. In the method, the user may chose any comfortable position for personally digitally locating their cervix and handling the apparatus of the invention and sampling tools. Successful positions include standing with both feet on the floor, standing with one foot resting on a raised surface, reclining, or laying on a bed.

Figure 10:
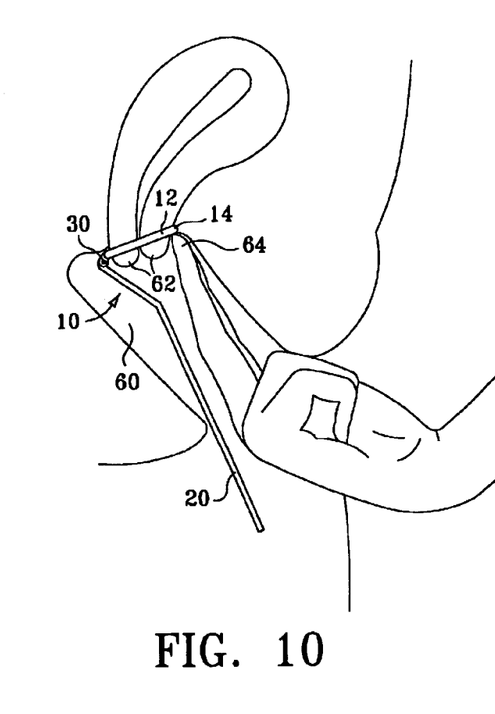
FIG. 10 is a side view of an embodiment of the present invention shown in FIG. 9, depicting the guide ring digitally raised into the sampling position around the user's cervix.

Referring to FIGS. 9–12, the user inserts the cervical guide tool 10 with guide ring 12 in the folded position, through the introitus 60 of the user's vagina until hinge mechanism 30 rests below the user's cervix 62. Proper positioning is confirmed by digital 64 location of the cervix 62 by the user. Next, the user raises ring 12 to a substantially vertical position until it encircles and captures the user's cervix 62. The user may check that ring 12 is properly engaged into position by pressing on ring 12 near upper section 14 as shown in FIG. 10.

Figure 11:
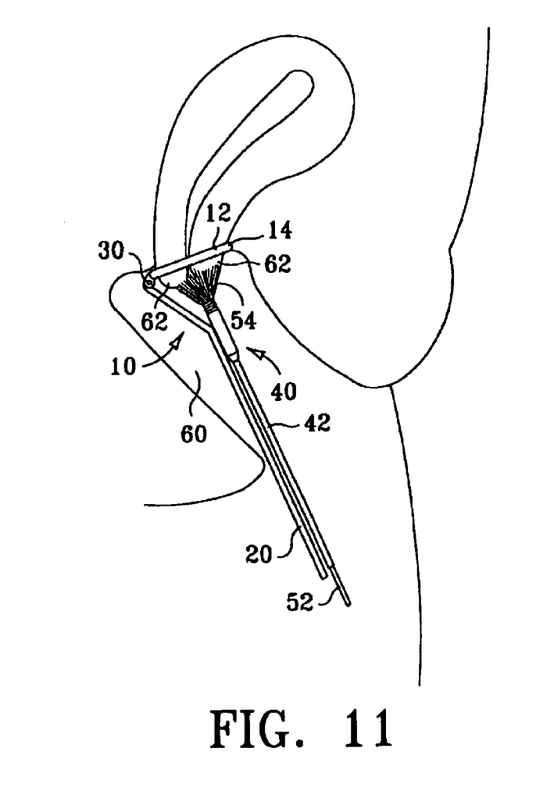
FIG. 11 is a side view of an embodiment of the present invention shown in FIG. 9, depicting a sampling tool adjacent to the cervix for collection of a tissue sample.

Referring back to FIGS. 5–7 in conjunction with FIG. 11, a sampling tool such as brush 50 is guided through the introitus 60 to cervix 62. Specifically, brush 50 is initially retracted in housing 41 of tool assembly 40. Slide mechanism 42 is engaged with longitudinal groove 26 at opening 28 and moved forwarded to stop 29. The user next advances collection bristles 54 out of brush housing 41 to the cervix 62 where rotating the bristles 54 gently against the cervix 62 assures collection of an adequate sample.

Figure 12:
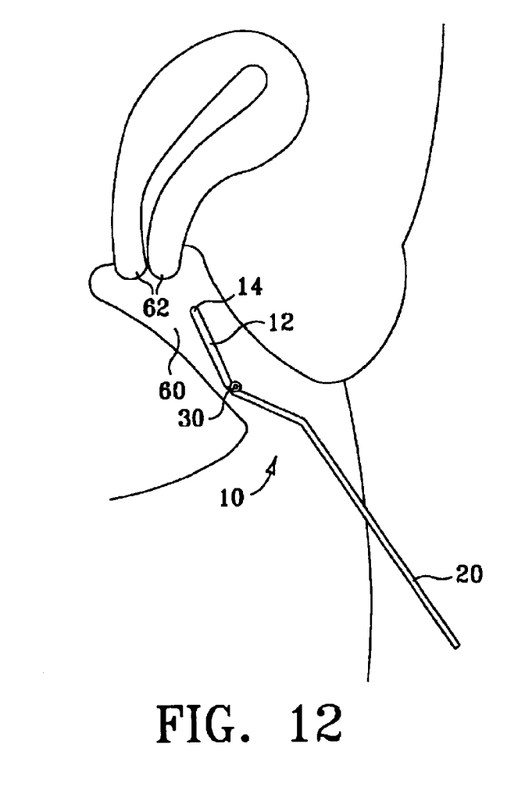
FIG. 12 is a side view of an embodiment of the present invention shown in FIG. 9, with the guide ring in the substantially horizontal position for removal.

The user next retracts the brush 50 into protective housing 41, removes the sampling tool assembly 40 from the vagina and repeats the process with additional sampling tools (not shown) as needed. Additional or alternative sampling tools known in the art for collection of tissue samples in the endocervical canal and surrounding surface area may be used as part of sampling tool assembly 40. Upon completion of the sampling process, the cervical guide apparatus 10 is next withdrawn. As shown in FIG. 12, the user pulls on handle 20 of apparatus 10 causing guide ring 12 to move to a substantially horizontal position for easy removal of the apparatus 10 from the user's vagina.

The tissue samples may be handled in any number of conventional ways known in the art. For example, the brush 50 of the sampling tool assembly 40 may be sealed in a fixative and sent to a lab, gynecologist or pathologist for interpretation of the samples.

Figure 13:
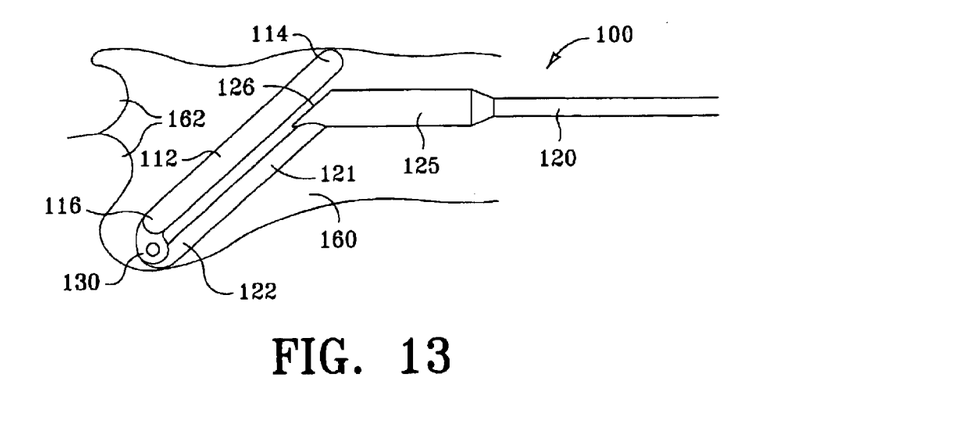
FIG. 13 is a side view of another embodiment of the present invention shown inserted in the user's vagina, having the guide ring in the folded, insertion position, and sampling tool housing within the insertion handle.
Figure 14:
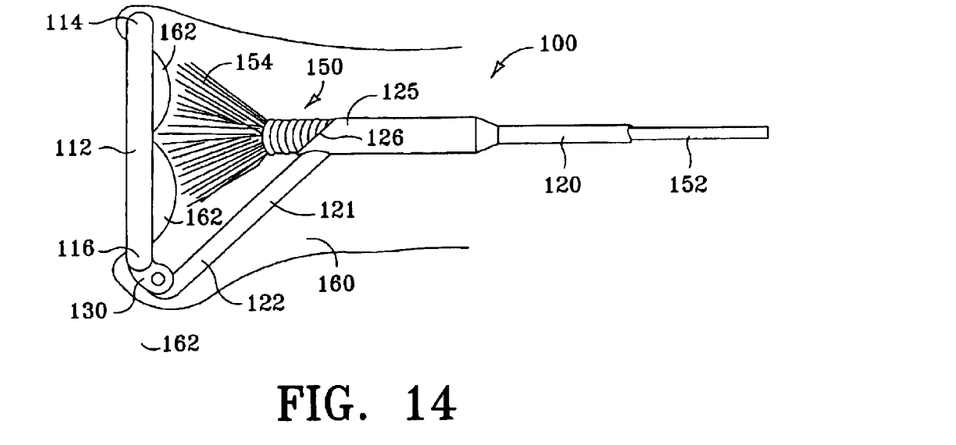
FIG. 14 is a side view of the embodiment of the present invention shown in FIG. 13, with the guide ring raised into position around the user's cervix and the sampling tool extended from the housing and adjacent to the user's cervix for collection of a tissue sample.

In FIGS. 13–14, another embodiment of the collection apparatus 100 is shown having an alternative means for guiding a tissue sampling tool to the user's cervix. Cervical guide apparatus 100 is shown folded within vaginal canal 160, proximal to cervix 162. In this embodiment, guide ring 112 includes upper section 114, lower section 116, hinge mechanism 130, and hollow handle 120. Handle 120 further includes protective tool housing 125, and slanted extension 121 proximal to handle end 122.

In FIG. 14, ring 112 is shown in the vertical sampling position, and sampling tool brush 150 having handle 152, is shown extended from the housing 125 through handle aperture 126, with bristles 154 adjacent to cervix 162 for tissue collection. Extension 121, when sufficiently angled between housing 125 and hinge mechanism 130, properly align and guide the collection bristles 154 to the endocervical canal and walls of cervix 162. In this embodiment, housing 125 serves the additional function of protecting the bristles 154 of sampling tool 150 from contamination during vaginal insertion and removal of collection apparatus 100.

Figure 15:
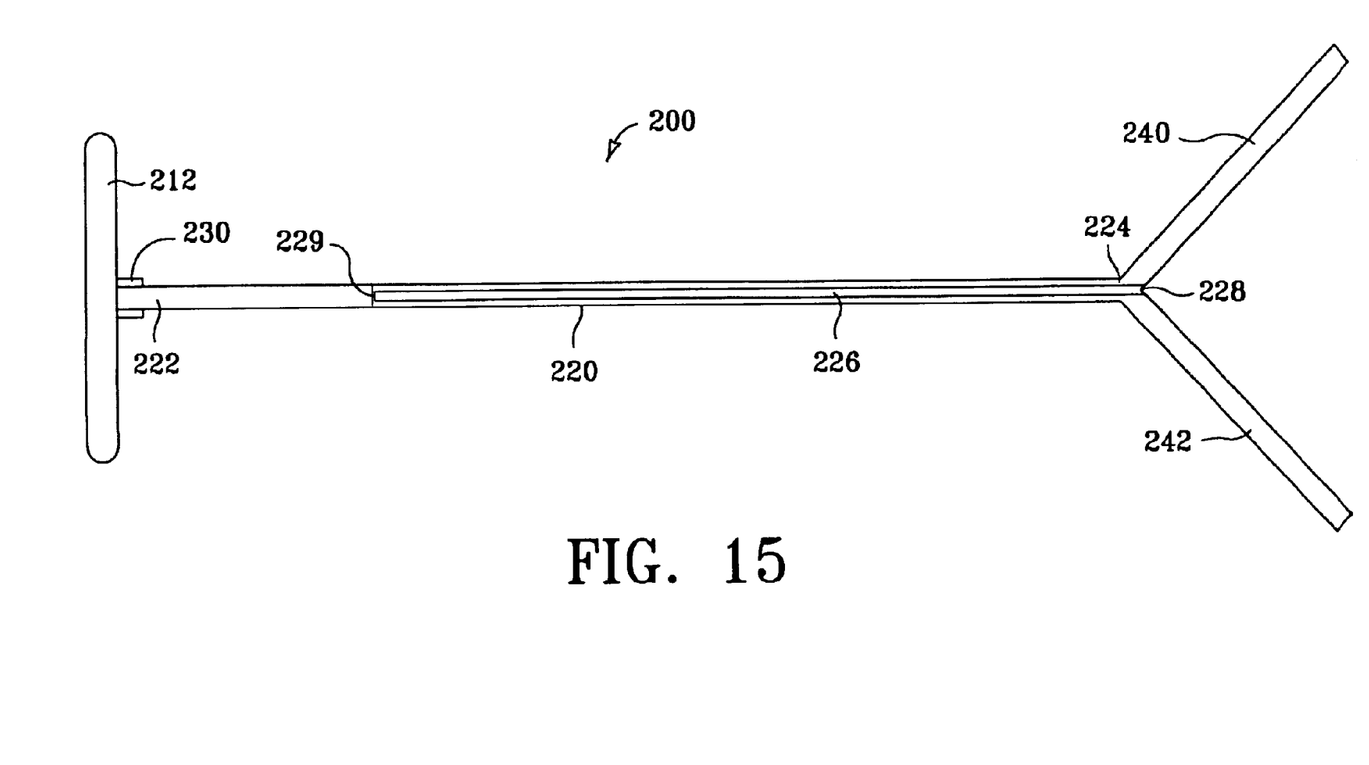
FIG. 15 is a plan view of an alternative embodiment of the present invention depicting dove-tailed handles.

With reference to FIG. 15, another feature of the present invention is shown on collection apparatus 200. Cervical guide tool 200 includes handle 220, guide ring 212, hinge means 230, and longitudinal groove 226 between ends 222, and 224 having open end 228 and stop 229. Proximal to end 228 are dove-tailed handles 240, 242 which facilitate the ability of left and right handed users to securely hold ring 212 in position against the cervix during sampling.

It will be understood and appreciated by those skilled in the art that the apparatus of the present invention may be changed or modified using alternative mechanisms and materials known in the art without departing from the spirit and scope of the invention as defined in the following claims.

What is claimed is:

1. An apparatus for self-collection of cellular and other biological materials from a woman's cervix, comprising:

a cervical guide ring having a central aperture, to capture the woman's cervix and permit digital palpation of said cervix;

one insertion handle having a proximal first end, a distal second end, and a hinge means for movably attaching the cervical guide ring adjacent to said proximal first end;

a means for guiding a tissue sampling tool to the woman's cervix; and a means for protecting the sampling tool from contamination.

2. The collection apparatus of claim 1, wherein the means for guiding the sampling tool to the woman's cervix includes a longitudinal groove between the first and second ends of the insertion handle, a stop proximal to the first end of the insertion handle, and an extension which slidably mates with said longitudinal groove.

3. The collection apparatus of claim 2, wherein the extension is located on the sampling tool.

4. The collection apparatus of claim 2, further comprising a tool housing and the extension is located on said tool housing.

5. The collection apparatus of claim 1, wherein the hinge means for movably attaching the cervical guide ring adjacent to the first end of the insertion handle is a unidirectional ratchet mechanism.

6. A method for collection of a cellular or other biological material sample from the cervix of a woman, comprising the steps of:

inserting a cervical guide tool through the introitus of the user's vagina, said guide tool including an insertion handle, a cervical guide ring, and a means for movably attaching the ring to the insertion handle;

lifting the ring to a substantially vertical position to capture the user's cervix in the center of the ring;

digitally palpating the cervix to confirm proper capture of the cervix through the ring;

guiding a sampling tool through the introitus of the user's vagina to the cervix;

wiping the cervix with the sampling tool to collect a tissue sample;

removing the sampling tool from the user's vagina; and removing the cervical guide tool from the user's vagina.

7. The method of claim 6, wherein the step of guiding a sampling tool through the introitus of the user's vagina to the cervix, further comprises the step of:

slidably mating an extension on the sampling tool to a groove in the handle of the cervical guide tool.

8. The method of claim 6, further comprising the step of sealing the tissue sample in a fixative for later analysis.

9. The method of claim 6, wherein the step of guiding a sampling tool through the introitus of the user's vagina to the cervix, further comprises the step of:

slidably mating an extension on a protective housing for said sampling tool to a groove in the handle of the cervical guide tool.

10. An apparatus for self-collection of cellular and other biological materials from a woman's cervix, comprising:

a cervical guide ring having a central aperture, to capture the woman's cervix and permit digital palpation of said cervix;

a hollow insertion handle having a first end, a second end, and a slanted extension proximal to said first end;

a hinge means for movably attaching the cervical guide ring adjacent to said first end; and a means for guiding a tissue sampling tool to the woman's cervix.

11. The collection apparatus of claim 10, wherein the hinge means for movably attaching the cervical guide ring adjacent to the first end of the insertion handle is a unidirectional ratchet mechanism.

* * * * *